United States Patent [19]
Sanders et al.

[11] Patent Number: 5,913,816
[45] Date of Patent: Jun. 22, 1999

[54] INTUBATION DEVICE AND METHOD

[75] Inventors: Gary H. Sanders, Rancho Santa Margarita; Frank Bowers, Irvine; Aaron Ingle, Laguna Beach; Dennis Constantinou, Corona del Mar; Guy R. Lowery, San Juan Capistrano; Malcolm D. Heaven, Laguna Hills, all of Calif.

[73] Assignee: Imagyn Medical Technologies, Inc., Newport Beach, Calif.

[21] Appl. No.: 08/963,593

[22] Filed: Oct. 31, 1997

[51] Int. Cl.⁶ ........................................... A61B 1/04
[52] U.S. Cl. .......................... 600/120; 600/114; 600/160; 600/156
[58] Field of Search ..................... 600/120, 146, 600/150, 160, 176, 121, 109, 194, 153, 114, 156; 128/200.26, 207.14

[56] References Cited

U.S. PATENT DOCUMENTS

| | | |
|---|---|---|
| 3,669,098 | 6/1972 | Takahashi . |
| 3,677,262 | 7/1972 | Zukowski . |
| 3,776,222 | 12/1973 | Smiddy . |
| 3,913,568 | 10/1975 | Carpenter . |
| 4,041,936 | 8/1977 | Carden . |
| 4,086,919 | 5/1978 | Bullard . |
| 4,360,008 | 11/1982 | Corazzelli, Jr. . |
| 4,567,882 | 2/1986 | Heller . |
| 4,580,556 | 4/1986 | Kondur . |
| 4,742,819 | 5/1988 | George . |
| 4,773,394 | 9/1988 | Reichstein et al. . |
| 4,795,430 | 1/1989 | Quinn et al. . |
| 4,846,153 | 7/1989 | Berci . |
| 4,900,306 | 2/1990 | Quinn et al. . |
| 4,981,471 | 1/1991 | Quinn et al. . |
| 4,982,729 | 1/1991 | Wu . |
| 5,016,614 | 5/1991 | MacAllister . |
| 5,174,283 | 12/1992 | Parker . |
| 5,183,031 | 2/1993 | Rossoff . |
| 5,203,320 | 4/1993 | Augustine . |
| 5,327,881 | 7/1994 | Greene . |
| 5,337,735 | 8/1994 | Salerno . |
| 5,339,805 | 8/1994 | Parker . |
| 5,363,838 | 11/1994 | George . |
| 5,365,940 | 11/1994 | Teves . |
| 5,400,771 | 3/1995 | Pirak et al. . |
| 5,431,152 | 7/1995 | Flam et al. . |
| 5,551,946 | 9/1996 | Bullard . |
| 5,607,386 | 3/1997 | Flam . |
| 5,620,408 | 4/1997 | Vennes et al. . |
| 5,643,174 | 7/1997 | Yamamoto et al. . |
| 5,645,519 | 7/1997 | Lee et al. . |
| 5,665,052 | 9/1997 | Bullard . |
| 5,676,635 | 10/1997 | Levin . |

*Primary Examiner*—Beverly M. Flanagan
*Attorney, Agent, or Firm*—Burns, Doane, Swecker & Mathis, L.L.P.

[57] ABSTRACT

An intubation device comprises an imaging conduit including an illumination conduit for delivering illumination to a distal end of the device and an image-receiving conduit for communicating images from the distal end of the device to the proximal end of the device. The device also comprises a flushing conduit for delivery of fluids and/or gases to the distal end of the device. The image conduit and the flushing conduit are attached at the distal end of the device. The distal end of the device can be manipulated by advancing the imaging conduit in an axial direction while maintaining the flushing conduit fixed in place. Furthermore, a length adjustment member is provided for adjusting the extent to which the distal end of the device extends beyond a distal end of an endotracheal tube which is inserted over the imaging and flushing conduits. The illuminating conduit and the image-receiving conduit terminate in separate ports at the distal end of the device. Furthermore, a substantial portion of the device is disposable, so that time consuming sterilization is not necessary.

29 Claims, 6 Drawing Sheets

INTUBATION DEVICE AND METHOD

BACKGROUND

The invention relates to an endoscope for use in an intubation procedure, and more particularly, to an endoscope designed for insertion into an endotracheal tube during an intubation procedure.

Many medical procedures require insertion of an endotracheal tube into the trachea of a patient. The endotracheal tube ensures proper ventilation in the patient, and also allows for the delivery of various gases to the patient, such as an anesthetic or oxygen.

In an intubation procedure, the endotracheal tube is typically introduced through the mouth of the patient. Simultaneously, a laryngoscope blade can be used to move the patient's tongue so that the patient's epiglottic and vocal cords can be viewed by the operator. The endotracheal tube is then advanced until it is positioned at the proper location in the patient's trachea. Once the endotracheal tube is properly positioned, a cuff affixed to the endotracheal tube can be inflated. This cuff seals the patient's airway passage to the flow of ambient gases, and also firmly fixes the endotracheal tube in place in the patient's trachea. At this time, the laryngoscope can be withdrawn leaving the endotracheal tube in the body.

In ideal situations, the above-described technique provides an adequate means for inserting an endotracheal tube in the patient's airway passage. However, the patient's airway passage may be obscured by blood or vomitus. Also, the patient's airway passage may be difficult to view due to anatomical features peculiar to the patient, such as an abnormally large tongue, tumors in the airway passage, trauma to the throat area, or various dental abnormalities (such as abnormally large or protruding teeth). These factors make it difficult for the operator to steer the endotracheal tube away from sensitive parts of the patient's airway passage, such as the vocal chords. Furthermore, these problems are compounded by the fact that intubation procedures are often performed in hectic emergency situations in which quick action is required.

Practitioners in this field have addressed this challenge through the use of various endoscopic visualization techniques. U.S. Pat. No. 4,846,153 to Berci exemplifies one such technique. This patent discloses a flexible endoscope which passes through the lumen of an endotracheal tube such that the tip of the endoscope is positioned in proximity to the distal end of the endotracheal tube. The tip of the endoscope contains an imaging element which communicates images from the distal end of the endoscope to the proximal end of the endoscope, and then to a portable monitor. The images displayed on the monitor can be viewed by the operator during insertion of the endotracheal tube, and thereby can be used to ensure that none of the sensitive structure in the patient's airway passage is damaged during the procedure. To maneuver the endotracheal tube away from such sensitive structures, the device additionally includes a steering mechanism. Other patents which disclose visualization techniques for use in intubation procedures are U.S. Pat. Nos. 5,363,838, 4,742,819, 3,776,222, and 4,567,882.

While the use of the above-described techniques and devices reduces the potential for damage to the sensitive structure in a patient's airway passage, there remains ample room for improvement in this field. More specifically, in addition to accuracy, it is desirable to provide an intubation device which is easy to use. Here, "ease of use" has various dimensions. First, the operator should be able to learn how to use the device in a relatively short period of time. It is desirable to make the device as straightforward as possible to accommodate especially those operators having limited training and experience. Second, the operator should be able to deploy the device quickly, and maneuver the device with accuracy and minimal effort. This is required because the device is often used in emergency situation in which quick action is demanded.

An intubation device should also be relatively easy to prepare for subsequent uses. This requirement includes ensuring that equipment is sterile upon each use. As the complexity of the device increases, the device often proves more difficult to sterilize due to, for instance, the fact that the device employs a larger and more complex surface area.

Finally, the commercial success of the device depends heavily on the expense at which it can be produced. The availability of sophisticated endoscope visualization techniques is of little use if this technology cannot be made available to the medical community at a manageable cost.

The above-mentioned patents fall short with regard to one or more of the above-stated requirements. Hence, it is an exemplary objective of the present invention to provide, at a reasonable expense, an intubation device which is easy to use and easy to prepare for reuse.

SUMMARY

These and other exemplary objectives are achieved according to the present invention through a device for use in an intubation procedure. According to a first exemplary embodiment, the device comprises a handle and a manipulation member movably attached to the handle. A flushing conduit is provided having a proximal end affixed to the handle, and having a distal end affixed to an endoscope tip. An imaging conduit is also provided having a proximal end affixed to the manipulation member, and having a distal end affixed to the endoscope tip. Actuation of the manipulation member causes movement of the imaging conduit relative to the flushing conduit, causing deflection of the endoscope tip.

According to another aspect of the first embodiment, the imaging conduit includes at least a first portion and a second portion, wherein the first portion is more rigid than the second portion. The second portion is located closer to the distal end of the device than the first portion. The first portion is more rigid than the second portion due to a tubular member which is disposed over the first portion, but not over the second portion. Alternatively, the first portion is more rigid than the second portion due to a rigid member, such as a metal rod, which is attached to the first portion, but not the second portion. A malleable member can also be disposed in the imaging conduit which maintains the shape it is bent to assume.

According to a second exemplary embodiment, the device comprises a handle and a length-adjustment threaded member attached to a distal end of the handle. An adjustment nut is attached to the handle which engages the length-adjustment threaded member. A mounting member is attached to a distal portion of the length-adjustment threaded member for use in attaching an endotracheal tube to the handle. Rotation of the adjustment nut causes movement of the mounting member toward or away from the handle.

According to a third exemplary embodiment, the device comprises an illumination conduit for delivering illumination to the distal end of the device and an image-receiving conduit for delivering images received from the distal end of the device. The illumination conduit and the image-receiving conduit terminate at separate ports at the distal end of the device.

According to additional aspects of the third embodiment, the image-receiving conduit includes a CCD element, an imaging chip element, a lens, or any combination of these elements. Images received at the distal end of the device can be communicated to the proximal end of the device using fiber optics or electrical wire, depending on whether the images are optically or electrically received at the distal end.

According to a fourth embodiment, an intubation assembly for use in an intubation procedure is provided. The assembly comprises an endotracheal tube, a handle, and a length-adjustment threaded member attached to a distal end of the handle. An adjustment nut is attached to the handle which engages the length-adjustment threaded member. A mounting member is attached to a distal portion of the length-adjustment threaded member for use in attaching the endotracheal tube to the handle. Rotation of the adjustment nut causes movement of the mounting member toward or away from the handle. The mounting member includes a locking nut for affixing the endotracheal tube to the handle.

According to a fifth embodiment, a method is provided for inserting an endotracheal tube into the trachea of a patient using an intubation device providing endoscope visualization, comprising the steps of: attaching the endotracheal tube onto the intubation device; adjusting a position of a distal portion of the endotracheal tube relative to an endoscope tip of the intubation device; inserting the endotracheal tube into the trachea of a patient using the intubation device by observing the location of sensitive structure in the patient's airway passage using the endoscope visualization provided by the intubation device; and removing the intubation device, leaving the endotracheal tube inserted in the patient's trachea.

According to a sixth embodiment of the invention, a method for inserting an endotracheal tube into the trachea of a patient is provided using an intubation device with endoscope visualization using imaging elements disposed in an image-receiving conduit of the intubation device, comprising the steps of: attaching the endotracheal tube onto the intubation device; inserting the endotracheal tube into the trachea of a patient using the intubation device by observing the location of sensitive structure in the patient's airway passage using the endoscope visualization provided by the intubation device; and removing the intubation device, leaving the endotracheal tube inserted in the patient's trachea; and disposing of the intubation device, with the exception of the imaging elements disposed in the image-receiving conduit.

BRIEF DESCRIPTION OF THE DRAWINGS

The foregoing, and other, objects, features and advantages of the present invention will be more readily understood upon reading the following detailed description in conjunction with the drawings in which.

DETAILED DESCRIPTION

In the following description, for purposes of explanation and not limitation, specific details are set forth in order to provide a thorough understanding of the invention. However it will be apparent to one skilled in the art that the present invention may be practiced in other embodiments that depart from these specific details. In other instances, detailed descriptions of well-known procedures and devices are omitted so as not to obscure the description of the present invention with unnecessary detail. In the drawings, like numerals represent like features.

1. Overview

Figure 1:
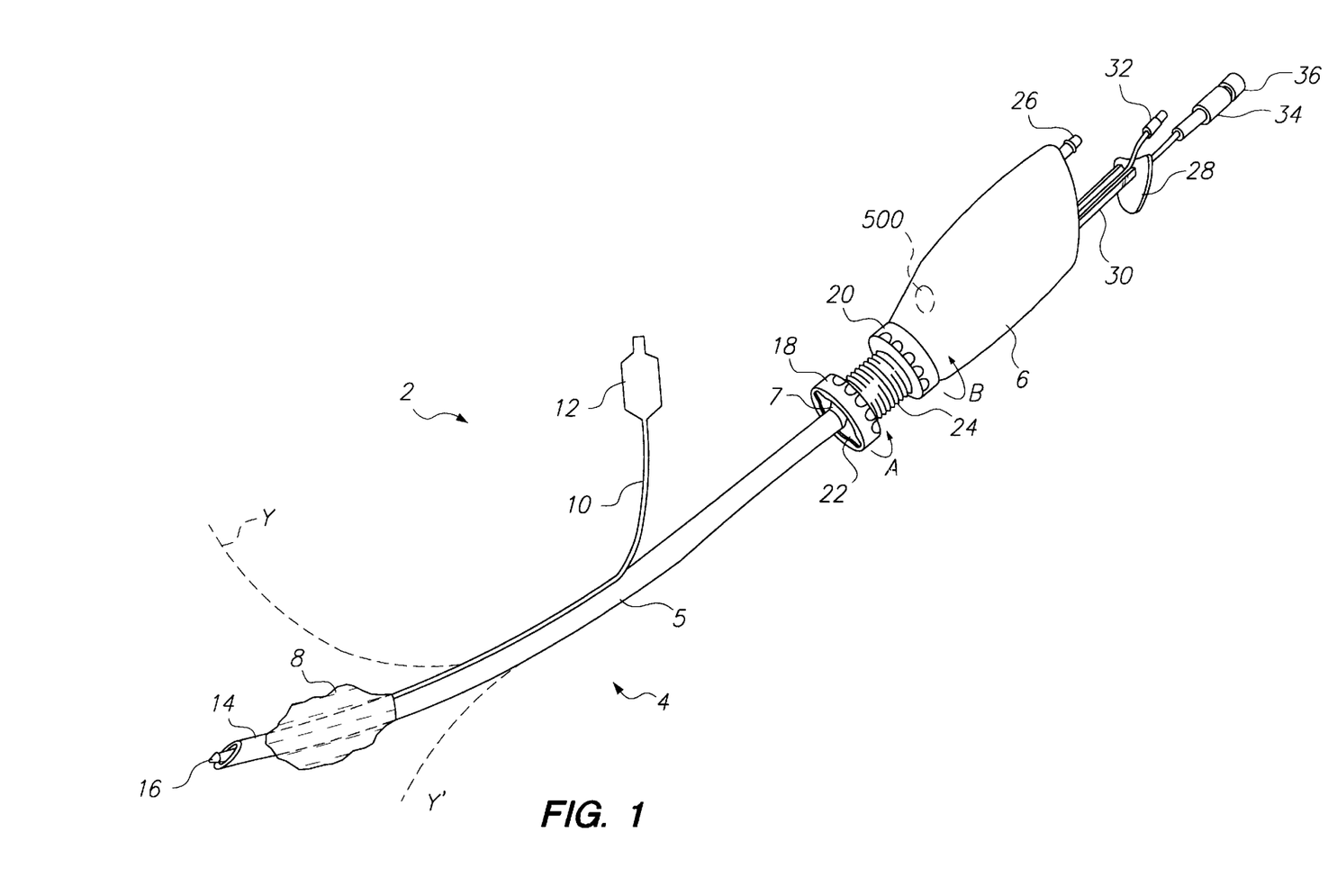
FIG. 1 shows an intubation device with an endotracheal tube attached thereto.

FIG. 1 shows an overview of the intubation device 2 according to one embodiment of the present invention. The intubation device 2 generally includes a handle section 6 by which the device is grasped during use. The handle includes a flushing port 26 for introducing fluids and/or gases to a flushing conduit (not shown in FIG. 1). The device 2 also includes an illumination port 32 for delivering electromagnetic radiation to an illumination conduit (not shown in FIG. 1). Finally, the device 2 includes an image-receiving port 34 for receiving images from an image-receiving conduit (not shown in FIG. 1). Both the flushing port 26 and the illumination port 32 include threaded end sections for providing connection to a standard fluid/gas delivery device and an electromagnetic generation device, respectively. The image-receiving port terminates in a locking nut 36 for securing a fiber optic bundle (or electrical wire) within the image-receiving conduit.

An endotracheal tube 4 extends from the handle 6. The endotracheal tube 4 includes a tubular section 5 comprised of a flexible material, such as a clear plastic material having sufficient rigidity to maintain the patient's airway passage open when inserted in the patient's trachea. The distal end of the tube 4 includes an inflation cuff 8. The cuff 8 comprises a standard distensible or inflatable bag or balloon. The cuff 8 can be inflated with fluids or gases such as air using a cuff distension device via a cuff distention connector 12 and distension conduit 10. The tube 4 terminates at its proximal end in a wing 7 which fits in locking engagement into the receiving slot 22 of locking nut 18.

The image-receiving conduit, illumination conduit and flushing conduit converge and are joined at the distal end of the device 2 at an endoscope tip 16. In one embodiment, the endoscope tip 16 protrudes a short distance beyond the distal end 14 of the tube 4. The position of the endoscope tip 16 and the distal end 14 of the tube 4 can be adjusted by rotating a length-adjusting nut 20. The length-adjusting nut 20 is rotationally affixed to the handle 6. Rotation of the length-adjusting nut 20 in a first direction advances a threaded length-adjustment member 24 away from the handle, which has the effect of advancing the distal end 14 of the tube past the endoscope tip 16. Rotation of the length-adjusting nut 20 in the opposite direction retracts the threaded length-adjustment member 24 into the handle 6, which has the effect of advancing the endoscope tip 16 out from the distal end 14 of the tube.

The image-receiving conduit and the illumination conduit are joined together to form an imaging conduit. The imaging conduit is attached to a thumb piece 28, which, in turn, is attached to a thumb piece extension member 30. Together, the thumb piece 28 and the thumb piece extension member 30 constitute a manipulation member. Depression of thumbpiece 28 pushes the imaging conduit toward the distal end of the device. The flushing conduit, on the other hand, is fixed to the handle 6. Also, as mentioned, the flushing conduit is joined to the illumination conduit and the image-receiving conduit (collectively forming the imaging conduit) at the endoscope tip 16. Thus, pressing on the thumb piece 28 pushes the endoscope tip 16 away from the handle 6 against the restraint of the flushing conduit which does not move. When the imaging conduit and the flushing conduit are confined to the lumen of the endotracheal tube 4, this action has the end result of bowing the distal portions of the tube 4. For instance, the end of the tube 4 can assume the curvature given by the dotted line "Y" shown in FIG. 1 when the thump piece 28 is actuated.

2. Tip Manipulation

Figures 2A, 2B:
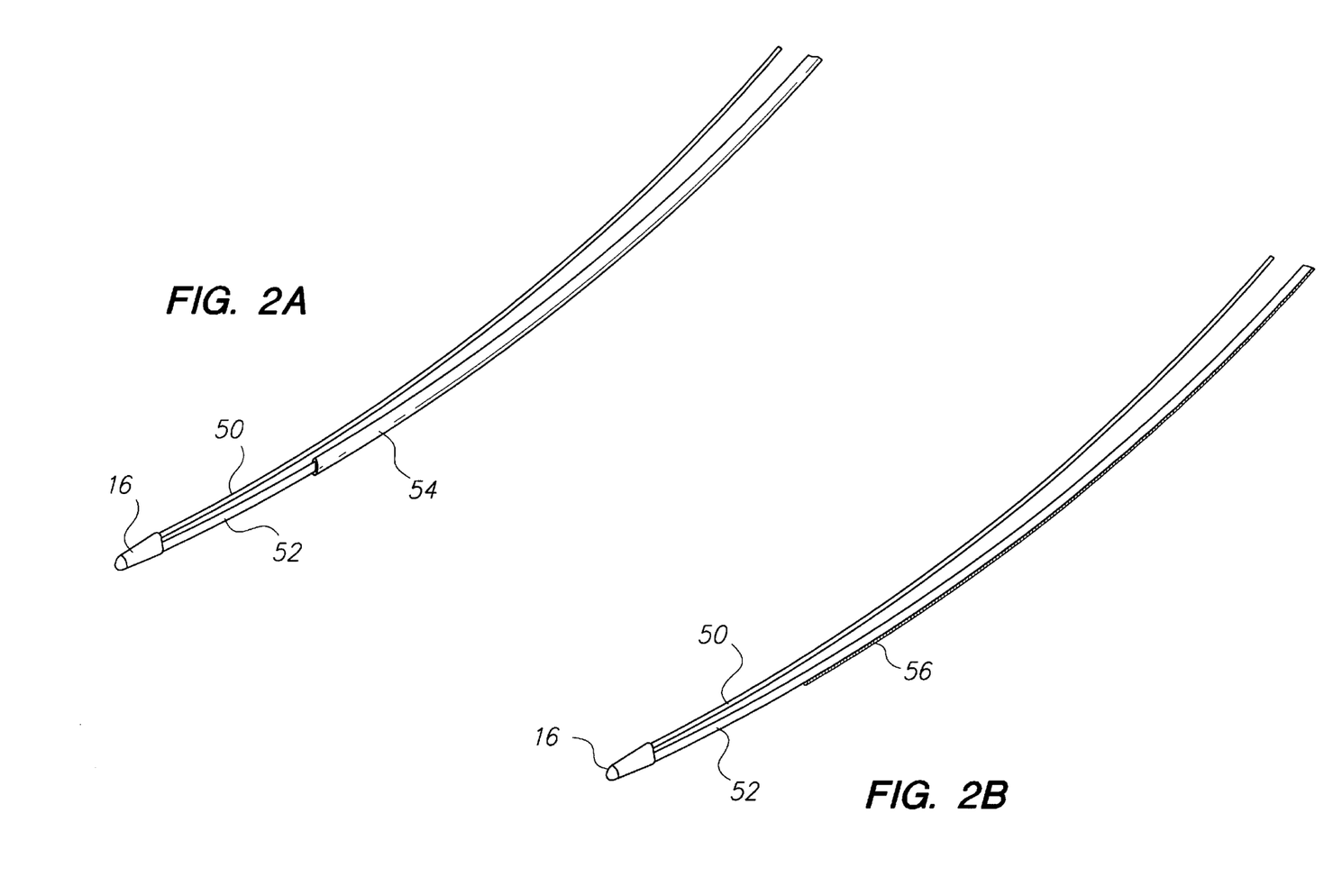
FIG. 2(a) shows a configuration of an imaging conduit and a flushing conduit according to one exemplary embodiment using a hollow tube to reinforce the rigidity of the imaging conduit.
FIG. 2(b) shows a configuration of an imaging conduit and a flushing conduit according to another exemplary embodiment using a wire to reinforce the rigidity of the imaging conduit.

The bending produced by actuation of the thumb piece 28 can be better understood by referring to FIGS. 2(*a*) and 2(*b*). FIG. 2(*a*), for instance, shows the configuration of the various conduits used in the intubation device without the endotracheal tube 4 disposed thereover. The conduits include a flushing conduit 50 and an imaging conduit 52. As mentioned above, the imaging conduit actually comprises two separate conduits—an illumination conduit and an image-receiving conduit. These conduits are joined at the endoscope tip 16. Further, a sheath 54 surrounds a substantial portion of the imaging conduit 52, leaving a prescribed portion of the distal end of the imaging conduit 52 uncovered. This sheath is made of a stiff plastic material, or other suitable material. The sheath has the effect of increasing the rigidity of the portion of the imaging conduit 52 that it covers. Thus, this rigidity-enhanced portion of the device will bend less readily than the uncovered portion of the imaging conduit 52 when the user depresses the thumb piece 28. This produces the curvature of the distal end of the tip generally along the line "Y" shown in FIG. 1. Of course, more acute curvatures can be obtained by pressing the thumb piece 28 with a stronger force, and less acute curvatures can be obtained by depressing the thumb piece 28 with a weaker force.

There are various ways to increase the rigidity of the imaging conduit 52 along prescribed portions of its length. For instance, a rod 56 having a desired stiffness can be affixed to a selected length of the imaging conduit 52, as shown in FIG. 2(*b*). The rod can comprises a metal wire, or a non-metallic strip of material (such as plastic). FIG. 2(*b*) shows the rod 56 attached to the exterior of the imaging conduit 52, but this rod can also be formed in the interior of the conduit (e.g., in one of the lumens of this conduit).

Alternatively, although not shown, the desired distribution of rigidity of the imaging conduit 52 can be achieved by molding or machining the imaging conduit 52 such that it has at least two ranges of thicknesses. For instance, the imaging conduit 52 can be made so that its distal end portion has a reduced thickness compared to the remainder of the conduit. This can be achieved by producing the imaging conduit in an extrusion process using two different extrusion dies for producing sections having corresponding different diameters. Still alternatively, the desired distribution of rigidity can be achieved by producing the imaging conduit using materials having different inherent rigidity. For instance, the proximal portion can be produced with a material having a higher rigidity compared to the distal portion.

According to yet another embodiment, the stiffness of the proximal portion of the imaging conduit can be increased by inserting a tube inside the image-receiving conduit or the illumination conduit, or both the image-receiving conduit and the illumination conduit. For instance, in FIG. 2(*a*), an internal tube can span the same length of the imaging conduit as the outer shell 54. The tube (or tubes) can be used in conjunction with the outer shell 54 (or some other stiffening mechanism), or without the outer shell. Each internal tube has an outer diameter slightly smaller than the inside diameter of the lumen in which it is inserted.

The tube can be formed of any material of suitable rigidity. For instance, the tube can be comprised of a malleable metallic material. In this case, the imaging conduit with this tube disposed therein can be bent to a desired shape and the imaging conduit will retain this shape. Alternatively, the tube can have resiliency. In this case, the imaging conduit with this tube disposed therein will spring back to its original shape when bent. Generally, the imaging conduit can use a combination of the above-described techniques to provide a desired combination of resiliency and deformability.

Those skilled in the art will appreciate that different types of curvatures can be achieved by varying the rigidity of the imaging conduit 52 along different portions of its length. Generally, as the rigidity-enhanced section of the imaging conduit 52 advances to encompass more of the distal end of the device, a progressively "tighter" curvature will be provided (i.e., having a smaller radius).

3. Imaging System

Figure 3:
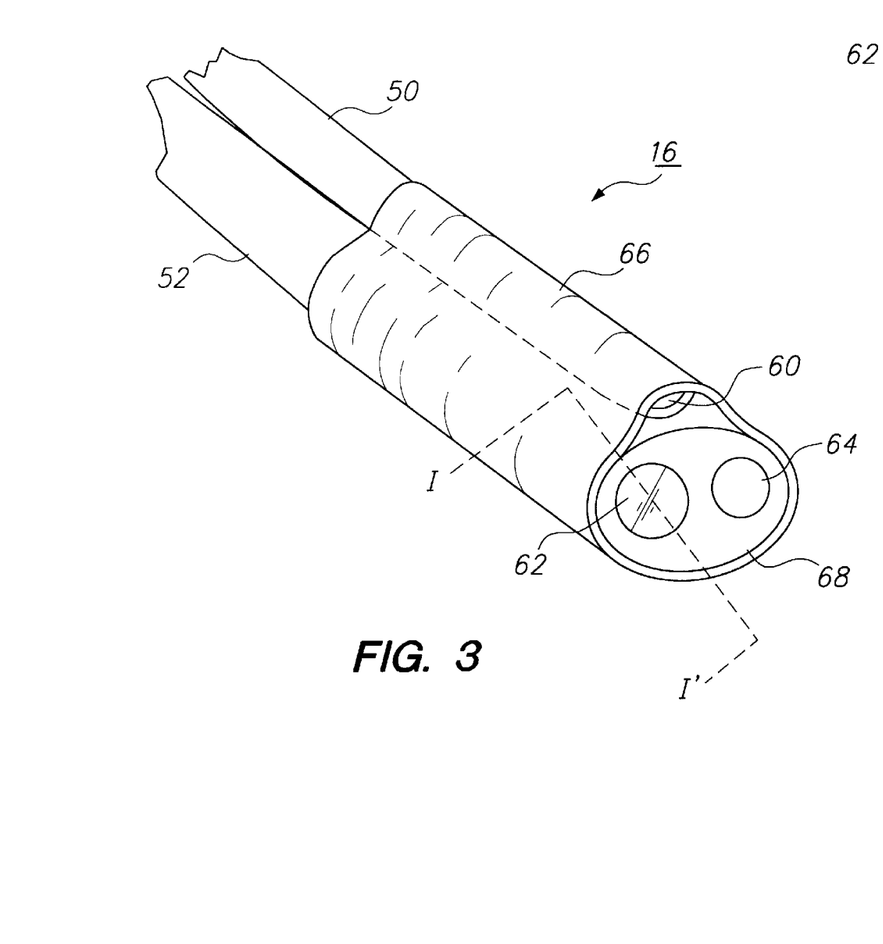
FIG. 3 shows a more detailed view of the distal end of the configurations shown in FIGS. 2(a) and 2(b)

As shown in FIG. 3, the imaging conduit 52 is joined to the flushing conduit 50 at the endoscope tip 16. One technique for joining these two conduits is by means of a plastic wrap 66 which is heat shrunk around the two conduits to tightly bind these two conduits together. However, those skilled in the art will appreciate that there are various ways to connect these two conduits, such as fusing these conduits together at some point in their manufacture, attaching the conduits together with adhesive, etc.

One function of the fluids and/or gases delivered by the flushing port is to flush away various secretions and obstructions which obscure the field-of-view of the endoscope. Thus, it is preferable to position the flushing port such that it is "aimed" at the field-of-view of the endoscope. For this reason, the flushing conduit 50 is connected to the imaging conduit 52 such that its outlet port 60 is retracted a short distance from the end of the imaging conduit 52. This ensures that the fluids and/or gases delivered by the flushing port do not "overshoot" the region directly in front of the imaging endoscope tip 16.

The terminal end of the imaging conduit 52 is also shown in FIG. 3. There are various possible designs that can be used to implement the imaging conduit 52. According to one design shown in FIG. 3, a dual-bored conduit is provided, wherein one bore constitutes the image-receiving conduit and the other bore constitutes the illumination conduit. In this case, region 68 would constitute a solid region, e.g., formed of plastic. The two-bored conduit is preferably formed by molding, but the bores can alternatively be formed by machining.

In another design, two separate lumens can be used to provide the image-receiving conduit and the illumination receiving conduit. These two conduits, in turn, can be bundled together in an outer shell. In this embodiment, the region 68 can comprise essentially empty space. It will be appreciated that the amount of this empty space can be decreased by ensuring that the outer shell fits the enclosed conduits snugly.

Whatever design is used, it is preferable that all reusable portions of the intubation device are kept sealed and separate from any portion of the device which comes in contact with the patient. For instance, it is contemplated that, in one embodiment, just the contents of the image-receiving conduit (e.g., including an imaging assembly) are reused. Thus, it is preferable that this portion of the system is separated from the patient. This can be ensured by sealing off the end of the image-receiving conduit with a window 62, which prevents the transmission of contaminants between the imaging assembly and the patient. After use, the entire intubation device except for the imaging assembly can be discarded.

The illumination conduit includes a light-transmission element 64, which can comprise a light pipe, an optical fiber, or like device. In one embodiment, the light-transmission element 64 is integrally attached to the imaging conduit, and thus is also discarded with the remainder of the intubation device. Alternatively, by separating the light-transmission element 64 from the patient, it is also possible to reuse the light-transmission element 64. This can be implemented by providing a window to separate the light-transmission element 64 from the external environment.

The use of separate ports for the image-receiving conduit and the light-transmission element 64 provides notable benefits over other known designs in which transmitted light and received images pass through a single window. For instance, when a single window is used, the images projected by the light-transmission element 64 can create reflections on the shared window, which may degrade the images captured by the imaging assembly of the image-receiving conduit. Since the present design uses two separate conduits for image-receiving and illumination, the reflected image problem can be minimized.

Figure 4A:
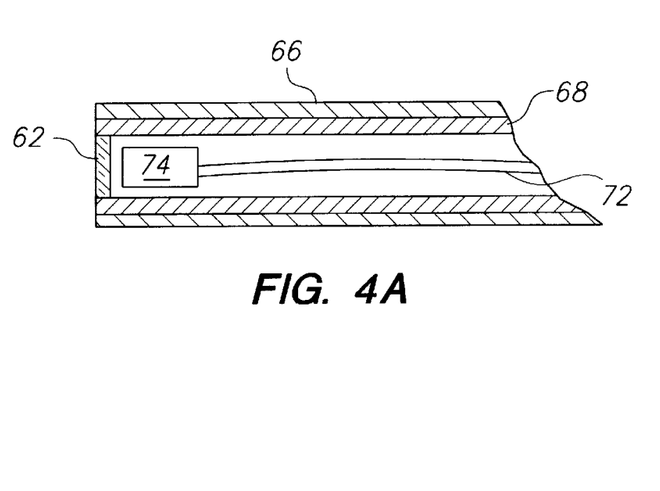
FIG. 4(a) shows a cross-section of the image-receiving conduit of the imaging conduit.

FIG. 4(a) shows a cross section of the image-receiving conduit used to communicate images from the distal end of intubation device to the proximal end of the endoscope device along the line I—I' shown in FIG. 3. As shown, the image-receiving conduit includes a window 62 comprised of a substantially transparent material. In one embodiment, a sapphire window can be used. The window is enclosed by the walls 68 of the dual-bored imaging conduit 52. In the case where the image-receiving conduit is allocated a separated tube (as opposed to the "double bore" design), the window 62 is enclosed by the walls of the image-receiving conduit. Alternatively, the window 62 can be secured to the end face of the imaging-receiving conduit 52.

Figure 4B:
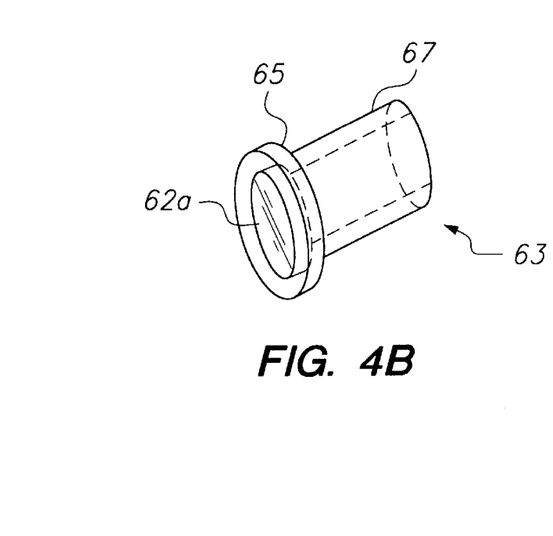
FIG. 4(b) shows a window insert for insertion into the image-receiving conduit.

In another design, shown in FIG. 4(b), a window insert 63 can be inserted into the distal end of the image-receiving conduit. The window insert includes a window 62a in its distal end. A first section 67 has a diameter sized such that the insert 63 fits snugly into the distal end of the image-receiving conduit. A second section 65 has a larger diameter. Accordingly, when the window insert 63 is fully inserted into the image-receiving conduit, the second section 65 abuts against the face of the imaging-receiving conduit. The window insert 63 can be formed of a suitable material, such as a plastic or metal (e.g., stainless steel).

The image-receiving conduit includes an image-receiving element 74 which communicates images to the proximal end of the device via cable 72. Together the element 74 and the cable 72 form an image-receiving assembly. The image-receiving element 74 can comprise a CCD (charge-coupled device) or other type of imaging chip (e.g., a CMOS imaging chip) which communicates its images in electronic form over an electrical wire to the proximal end of the intubation device.

In another embodiment, images can be captured at the distal end by an optical element, such as one or more lenses, and transferred to the proximal end of the device via a fiber optic cable. Alternatively, the element 74 can simply consist of the terminal end of a fiber optic cable (e.g., without a lens). Still alternatively, a light pipe can be used to transfer the images to the proximal end of the intubation device. Various combinations of these techniques can also be used. For instance, one or more lenses can be used in conjunction with a CCD device or chip.

The image-receiving element 74 need not be positioned in abutment with the window 62 since the light-transmission element 64 does not create reflections on the window 62 of the image-receiving conduit. In contrast, systems using a shared window for use by both a light-transmission element and an image-receiving element require placing the image receiving element in abutment with the window to minimize the effects of these reflections.

Although not shown, the dual-bored conduit can include one of more guides for seating the image-receiving element 74 in a prescribed position relative to the window 62. For instance, the dual-bored conduit can include an area of decreased diameter in proximity to the window 62. The diameter is sized such that the image-receiving element 74 is received and aligned in a prescribed position relative to the window 62 (e.g., such that the image-receiving element is held in abutment with the window 62 or is spaced a prescribed distance from the window 62).

4. The Endotracheal Tube Locking Nut

Figure 5A:
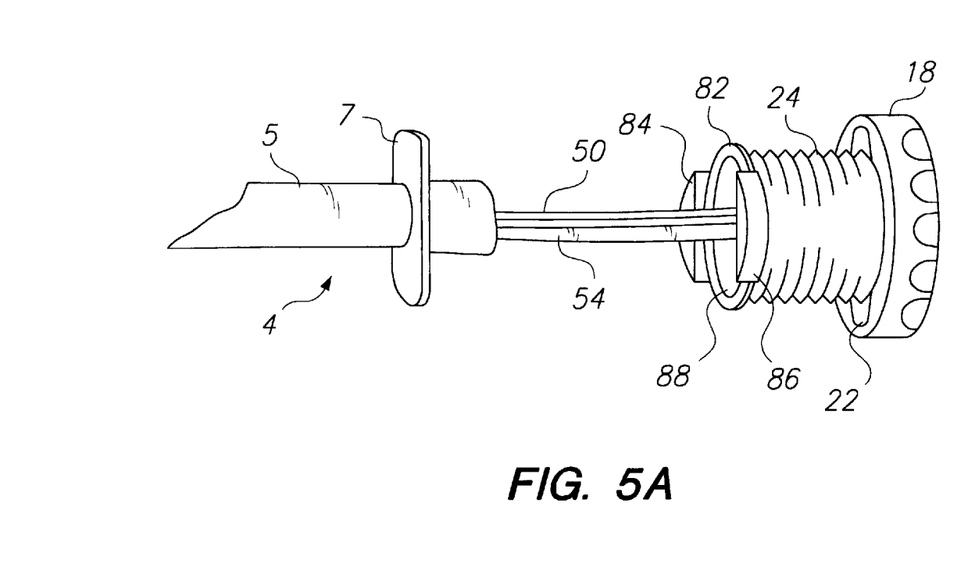
FIGS. 5(a), 5(b) and 5(c) illustrate the manner in which the endotracheal tube is fastened to the intubation device.
Figure 5B:
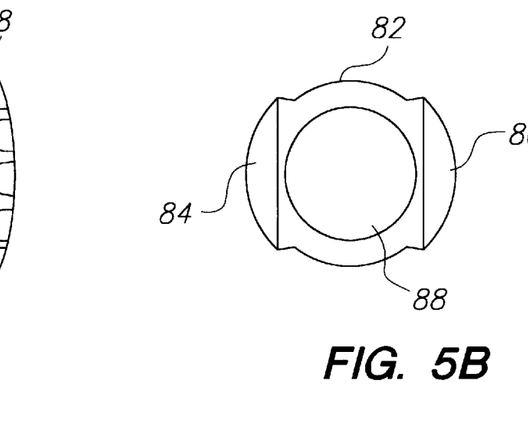
Figure 5C:
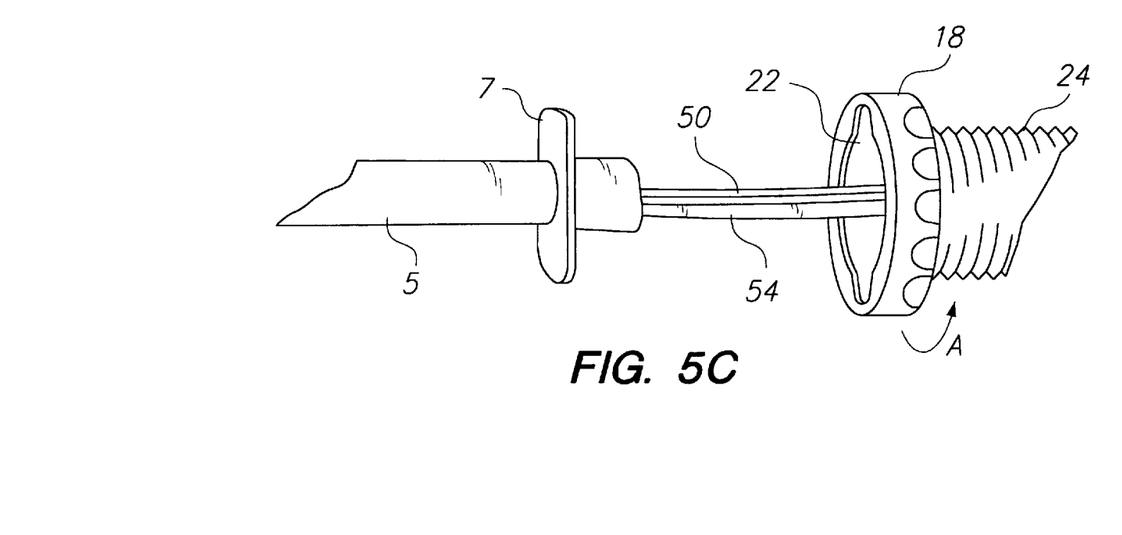

FIGS. 5(a), 5(b) and 5(c) show an exemplary method for attaching the endotracheal tube 4 to the handle 6. As shown in FIGS. 5(a) and 5(b), the terminal end of the threaded length-adjustment member 24 flares out into a ring portion 82 having a diameter larger than the diameter of the threaded length-adjustment member 24. Diametrically opposed flanges 84 and 86 extend outward from the ring 82. The flanges 84 and 86 include a curved outer edge and a linear inner edge. The area between the inner linear edges defines a slot. (Note that FIG. 5(b) shows a view of FIG. 5(a) looking at the ring 82 and the flanges 84 and 86 along the axial direction of the threaded length-adjustment member 24). The slot between the flanges 84 and 86 is sized to snugly receive the wing 7 of the endotracheal tube 4. The ring 82, the flanges 84 and 86, and the nut 18 collectively form a mounting member.

To attach the endotracheal tube 4 to the handle 6, the locking nut 18 is slid from its position shown in FIG. 5(a) to the position shown in FIG. 5(c). In this position, the elongated slot 22 formed in the face of the locking nut 18 is aligned in parallel with the slot formed between the flanges 84 and 86. In this configuration, the wing 7 can be inserted through the slot 22 in the nut 18 and then firmly seated in the slot formed between the flanges 84 and 86. At this time, the adjustment nut 18 is rotated a quarter of a turn, thereby locking the endotracheal tube 4 onto the handle 6.

Those skilled in the art will recognize that there are various alternative techniques for attaching the endotracheal tube 4 to the handle 6.

5. Handle-Side Features

Figures 6A, 7:
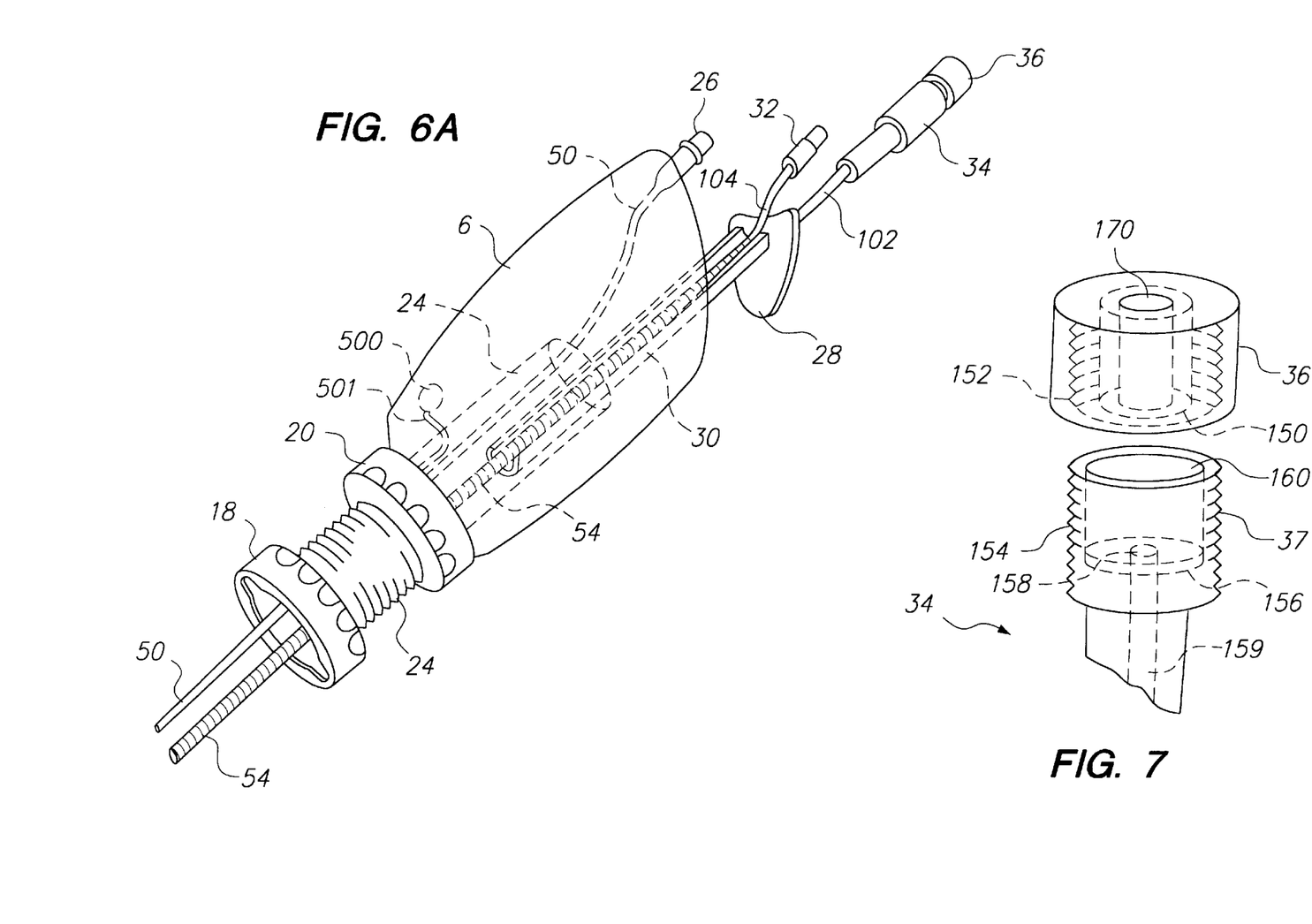
FIGS. 6(a), 6(b) and 6(c) illustrate an exemplary construction of the handle portion of the intubation device.
FIG. 7 shows a locking nut used to secure a fiber optic bundle (or electrical wire) within an image-receiving conduit of the imaging conduit.

FIG. 6(a) shows the structure housed inside the handle 6 (using dotted lines). As shown, the threaded length-adjustment member 24 extends into the handle 6. The sheathed imaging conduit 54 and the flushing conduit 50 extend through the threaded length-adjustment member 24. Upon exiting from the handle 6, the sheathed imaging conduit 54 splits into the illumination conduit 104 and the image-receiving conduit 102, which terminate in the ports 32 and 34, respectively.

Figure 6B:
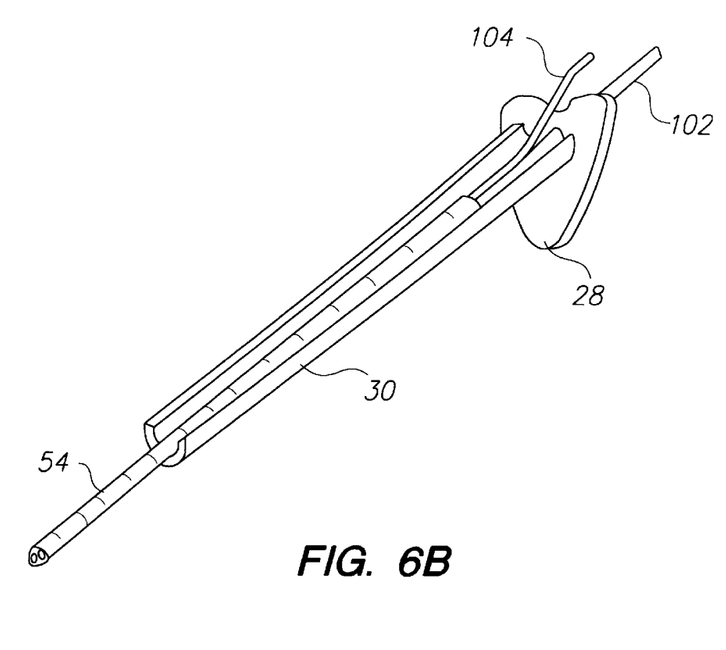

With reference to both FIGS. 6(a) and 6(b), a thumb piece extension member 30 extends from the thumb piece 28. In one exemplary embodiment, the thumb piece extension member forms a halved tube which cradles the sheathed imaging conduit 54. The sheathed imaging conduit 54 is fixed to the thumb piece extension member 30 by adhesive or other form of bonding. Accordingly, pressing on the thumb piece 28 advances the imaging conduit 54 toward the distal end of the endoscope. On the other hand, the flushing conduit 50 is held fixed to the handle 6. The force exerted on the imaging conduit 54 will thus cause a bowing in the imaging conduit, causing the distal end of the device to make an arc.

It is also possible to achieve the above-described bowing by pushing on the flushing conduit and holding the imaging conduit fixed in place. Furthermore, the conduits can be bundled together in alternative arrangements. For instance, the flushing conduit can be bundled with the illumination conduit, or the flushing conduit can be bundled with the image-receiving conduit. In yet another embodiment, all three conduits (the flushing, illumination and image-receiving conduit) can be bundled together, and a fourth conduit can be provided in the illustrated position of the flushing conduit. This fourth conduit can comprise a lumen for introducing medical instruments. Instead, a solid flexible rod can be used in place of this fourth conduit.

Furthermore, there are alternative ways to move the conduits with respect to each other. For instance, various types of levers, buttons, knobs, etc., can be used to move one conduit with respect to another. The invention also contemplates the use of a manipulation member which can pull on one conduit while holding another conduit fixed in placed, or can both pull and push on one conduit. This last embodiment can bend the distal end of the device in both directions Y and Y' shown in FIG. 1.

Figure 6C:
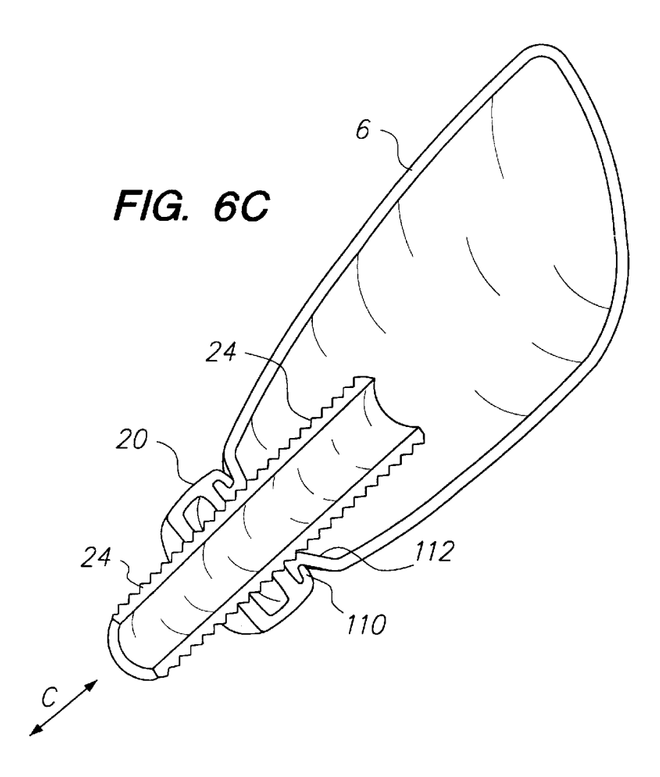

The position of the endoscope tip 16 relative to the distal end 14 of the endotracheal tube can be adjusted by rotating the length-adjustment nut 20. As shown in FIG. 6(c), the length-adjustment nut 20 has a lip 110 which engages and interlocks with a lip 112 of the handle 6. Furthermore, portions of the length-adjustment nut 20 are mated in threaded engagement with the length-adjustment member 24. Accordingly, when the length-adjustment nut 20 is rotated, the nut itself remains stationary, but the length-adjustment member 24 moves in the axial direction "C". Since the endotracheal tube 4 is mounted on the end of the length adjustment member 24, movement of the length-adjustment member 24 advances the distal end 14 of the endotracheal tube 4 relative to the endoscope tip 16.

FIG. 7 shows the exemplary configuration of the imaging receiving port 34. The port 34 includes a locking nut 36 having an internal threaded surface 152. The nut 36 also includes an internal post 150 having a central opening 170 for receiving a cable (e.g., an optical fiber or electrical wire). The port 34 also includes a second member 37 having an external threaded surface 154 for engagement with the internal threaded surface 152 of the locking nut 36. The member 37 also includes recess 160 for receiving the post 150. A resilient washer 156 is located at the bottom surface of the recess 160. A hole 158 in the washer 156 is concentric with a hole 159 in the member 37 and the hole 170 in the post 150.

In operation, a cable is threaded through the holes 170, 158 and 159. The threaded nut 36 is then tightened on the member 37. When the post 150 contacts the resilient washer 156 it deforms the washer 156, causing the diameter of the hole 158 to decrease, which, in turn, causes the resilient material of the washer to grip the cable. Thus, it is possible to firmly position the cable relative to the image-receiving conduit by tightening the nut 36 on the member 37. As mentioned, the cable can comprise either a fiber optic cable or an electrical wire.

As mentioned, gases and/or fluids can be introduced into the flushing conduit 50 via the flushing port 26. The gases and/or fluids exit the flushing conduit 50 at the port 60 (in FIG. 3). The gases and fluids serve the beneficial role of removing obstructions (such as blood, mucus, vomitus, etc.) from the field-of-view of the imaging conduit 52. According to another embodiment, these flushing gases and/or fluids can also be passed through the lumen of the endotracheal tube 4, outside the flushing and imaging conduits. This flow of gases and/or fluids can be introduced through an additional port 500 (shown in FIGS. 1 and 6(a)). A separate flushing conduit 501 (FIG. 6(a)) can be provided which connects this supplemental flushing port 500 with the lumen of the endotracheal tube 4 via the lumen defined by the interior of the length-adjustment member 24. The use of this optional flushing port offers the ability to deliver greater quantities of gases and/or fluids more directly to the source of the obstruction in the patient's airway passage. Thus, when the operator finds that the airway passage of the patient is heavily obscured with blood, mucus, vomitus, etc., the operator can detach the flushing supply from port 26 and attach the flushing supply to port 500 to remove the obstructions.

6. Method of Operation

In operation, the intubation device is prepared for use by attaching a fluid delivery apparatus and a light generation apparatus to the flushing conduit port 26 and the illumination conduit port 32, respectively. Also, the image-receiving conduit port 34 is connected to an input port of an image viewing apparatus, such as a conventional CRT monitor or LCD display.

The endotracheal tube 4 is then locked onto the handle 6 using the locking nut 18 as described above. The endoscope tip 16 can then be moved to a desired position relative to the distal end 14 of the endotracheal tube 5. For instance, it is common to position the endoscope tip 16 so that it barely protrudes beyond the end 14 of the endotracheal tube 4.

The intubation device 2 with the endotracheal tube 4 attached thereto can then be inserted into the mouth and airway passage of a patient. The operator advances the endotracheal tube 4 with the assistance of the intubation device 2, while observing the output monitor which shows the internal structure of the patient's airway passage. The tip 16 of the device can be maneuvered to avoid sensitive structure within the patient's airway passage by a combination of adjusting the position and orientation of the device and depressing the thumb piece 28. Once the endotracheal tube 4 is properly positioned, the intubation device 2 can be removed, leaving the endotracheal tube in place.

In one embodiment, the intubation device 2 is discarded after a single use, along with the used endotracheal tube. Thus, in one embodiment, the only portion of the intubating scope and endotracheal tube that is not disposable is the imaging assembly within the image receiving conduit. Of course, alternatively, the above-described device 2 can be re-used after proper sterilization.

The above-described exemplary embodiments are intended to be illustrative in all respects, rather than restrictive, of the present invention. Thus the present invention is capable of variations in detailed implementation that can be derived from the description contained herein by a person skilled in the art. For instance, the device can serve as general endoscope and can be utilized in other procedures besides intubation. All such variations and modifications are considered to be within the scope and spirit of the present invention as defined by the following claims.

What is claimed is:

1. A device for use in an intubation procedure comprising:
   a handle;
   a manipulation member movably attached to said handle;
   a flushing conduit having a proximal end affixed to said handle, and having a distal end affixed to an endoscope tip; and
   an imaging conduit having a proximal end affixed to said manipulation member, and having a distal end affixed to said endoscope tip;
   wherein actuation of said manipulation member causes movement of said imaging conduit relative to said flushing conduit, causing deflection of said endoscope tip.

2. The device according to claim 1, wherein said imaging conduit includes at least a first portion and a second portion, wherein said first portion is more rigid than said second portion.

3. The device according to claim 2, wherein said second portion is located closer to a distal end of said device than said first portion.

4. The device according to claim 2, wherein a tubular member is disposed over said first portion.

5. The device according to claim 2, wherein a rigid member is attached to said first portion.

6. The device according to claim 5, wherein the rigid member comprises a metal rod.

7. The device according to claim 1, wherein said imaging conduit includes an illumination conduit for delivering illumination to said endoscope tip and an image-receiving conduit for communicating images from said endoscope tip wherein said illumination conduit and said image-receiving conduit terminate at separate ports at the endoscope tip.

8. The device according to claim 1, further including:
   a length-adjustment threaded member attached to a distal end of said handle;
   an adjustment nut attached to said handle which engages said length-adjustment threaded member; and
   a mounting member attached to a distal portion of said length-adjustment threaded member for use in attaching an endotracheal tube to said handle;
   wherein rotation of said adjustment nut causes axial movement of said mounting member and an endotracheal tube attached thereto.

9. The device according to claim 1, wherein said device is formed substantially of a plastic material.

10. The device according to claim 1, wherein said imaging conduit comprises a dual-lumen conduit formed of molded plastic material.

11. A device for use in an intubation procedure comprising:
    a handle;
    a length-adjustment threaded member attached to a distal end of said handle;
    an adjustment nut attached to said handle which engages said length-adjustment threaded member; and
    a mounting member attached to a distal portion of said length-adjustment threaded member for use in attaching an endotracheal tube to said handle;
    wherein rotation of said adjustment nut causes movement of said mounting member toward or away from said handle.

12. The device according to claim 11, further including:
    a manipulation member movably attached to said handle;
    a flushing conduit having a proximal end affixed to said handle, and having a distal end affixed to an endoscope tip; and
    an imaging conduit having a proximal end affixed to said manipulation member, and having a distal end affixed to said endoscope tip;
    wherein actuation of said manipulation member causes movement of said imaging conduit relative to said flushing conduit, causing deflection of said endoscope tip.

13. The device according to claim 11, wherein said imaging conduit includes an illumination conduit for delivering illumination to said endoscope tip and an image-receiving conduit for communicating images from said endoscope tip, wherein said illumination conduit and said image-receiving conduit terminate at separate ports at the endoscope tip.

14. The device according to claim 11, wherein said device is formed substantially of a plastic material.

15. The device according to claim 12, wherein said imaging conduit comprises a dual-lumen conduit formed of molded plastic material.

16. A device for use in an intubation procedure comprising:
    an illumination conduit for delivering illumination to a distal end of said device;
    an image-receiving conduit for communicating images from said distal end of said device;
    wherein said illumination conduit and said image-receiving conduit terminate at separate ports at the distal end of the device, the device including:
    a handle;
    a manipulation member movably attached to said handle;
    a flushing conduit having a proximal end affixed to said handle, and having a distal end affixed to an endoscope tip; and
    an imaging conduit having a proximal end affixed to said manipulation member, and having a distal end affixed to said endoscope tip;
    wherein actuation of said manipulation member causes movement of said imaging conduit relative to said flushing conduit, causing deflection of said endoscope tip wherein said imaging conduit includes said illumination conduit and said image-receiving conduit.

17. The device according to claim 16, wherein said image-receiving conduit includes an imaging element positioned at the distal end of said device.

18. The device according to claim 17, wherein said imaging element comprises a CCD element.

19. The device according to claim 17, wherein said imaging element comprises an imaging chip.

20. The device according to claim 17, wherein said imaging element comprises one or more optical lenses.

21. The device according to claim 17, wherein an optical light pipe connects said imaging element at said distal end to the proximal end of said device.

22. The device according to claim 17, wherein an electrical wire connects said imaging element at said distal end to the proximal end of said device.

23. The device according to claim 17, wherein an optical fiber connects said imaging element at said distal end to the proximal end of said device.

24. The device according to claim 17, wherein said image-receiving conduit terminates in a window which separates said imaging element contained in said image-receiving conduit from a patient, so as to maintain a sterile boundary between said imaging element and said patient.

25. The device according to claim 16, wherein said image-receiving conduit terminates in a window comprised of a transparent material.

26. The device according to claim 25, wherein said transparent material is sapphire.

27. A device for use in an intubation procedure comprising:
   an illumination conduit for delivering illumination to a distal end of said device;
   an image-receiving conduit for communicating images from said distal end of said device;
   wherein said illumination conduit and said image-receiving conduit terminate at separate ports at the distal end of the device;
   a handle;
   a length-adjustment threaded member attached to a distal end of said handle;
   an adjustment nut attached to said handle which engages said length-adjustment threaded member; and
   a mounting member attached to a distal portion of said length-adjustment threaded member for use in attaching an endotracheal tube to said handle;
   wherein rotation of said adjustment nut causes movement of said mounting member toward or away from said handle.

28. An intubation assembly for use in an intubation procedure comprising:
   an endotracheal tube;
   a handle;
   a length-adjustment threaded member attached to a distal end of said handle;
   an adjustment nut attached to said handle which engages said length-adjustment threaded member; and
   a mounting member attached to a distal portion of said length-adjustment threaded member for use in attaching said endotracheal tube to said handle;
   wherein rotation of said adjustment nut causes movement of said mounting member toward or away from said handle.

29. The assembly according to claim 28, wherein said mounting member includes a locking nut for affixing said endotracheal tube to said handle.

* * * * *